(12) United States Patent  
Graumann

(10) Patent No.: US 8,374,678 B2  
(45) Date of Patent: Feb. 12, 2013

(54) MEDICAL APPARATUS WITH IMAGE ACQUISITION DEVICE AND POSITION DETERMINATION DEVICE COMBINED IN THE MEDICAL APPARATUS

(75) Inventor: Rainer Graumann, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1003 days.

(21) Appl. No.: 11/677,199

(22) Filed: May 7, 2007

(65) Prior Publication Data

US 2007/0238986 A1 Oct. 11, 2007

(30) Foreign Application Priority Data

Feb. 21, 2006 (DE) .................... 10 2006 008 042

(51) Int. Cl.
*A61B 5/055* (2006.01)
*A61B 6/08* (2006.01)
*G01D 18/00* (2006.01)

(52) U.S. Cl. ......... 600/424; 600/427; 378/205; 378/207

(58) Field of Classification Search ..................... None
See application file for complete search history.

(56) References Cited

U.S. PATENT DOCUMENTS

| 5,377,678 | A  | * | 1/1995 | Dumoulin et al. ............ 600/424 |
| 6,050,724 | A  |   | 4/2000 | Schmitz et al. |
| 6,527,443 | B1 |   | 3/2003 | Vilsmeier et al. |
| 6,574,296 | B2 | * | 6/2003 | Stierstorfer .................... 378/15 |
| 6,739,752 | B2 | * | 5/2004 | Sabczynski et al. .......... 378/207 |
| 6,895,268 | B1 |   | 5/2005 | Rahn et al. |
| 6,932,506 | B2 |   | 8/2005 | Mitschke et al. |
| 2004/0082854 | A1 | | 4/2004 | Essenreiter et al. |

FOREIGN PATENT DOCUMENTS

DE 101 09 310 A1 9/2002
DE 10 2004 001 858 A1 5/2005

* cited by examiner

*Primary Examiner* — Long V. Le
*Assistant Examiner* — Angela M Hoffa
(74) *Attorney, Agent, or Firm* — Schiff Hardin LLP

(57) ABSTRACT

In a medical apparatus for implementation of operative procedures on a patient, an image acquisition device and a position determination device combined and permanently associated in the medical apparatus. The position determination device serves for determination of the position of at least one medical instrument within an operation region.

7 Claims, 1 Drawing Sheet

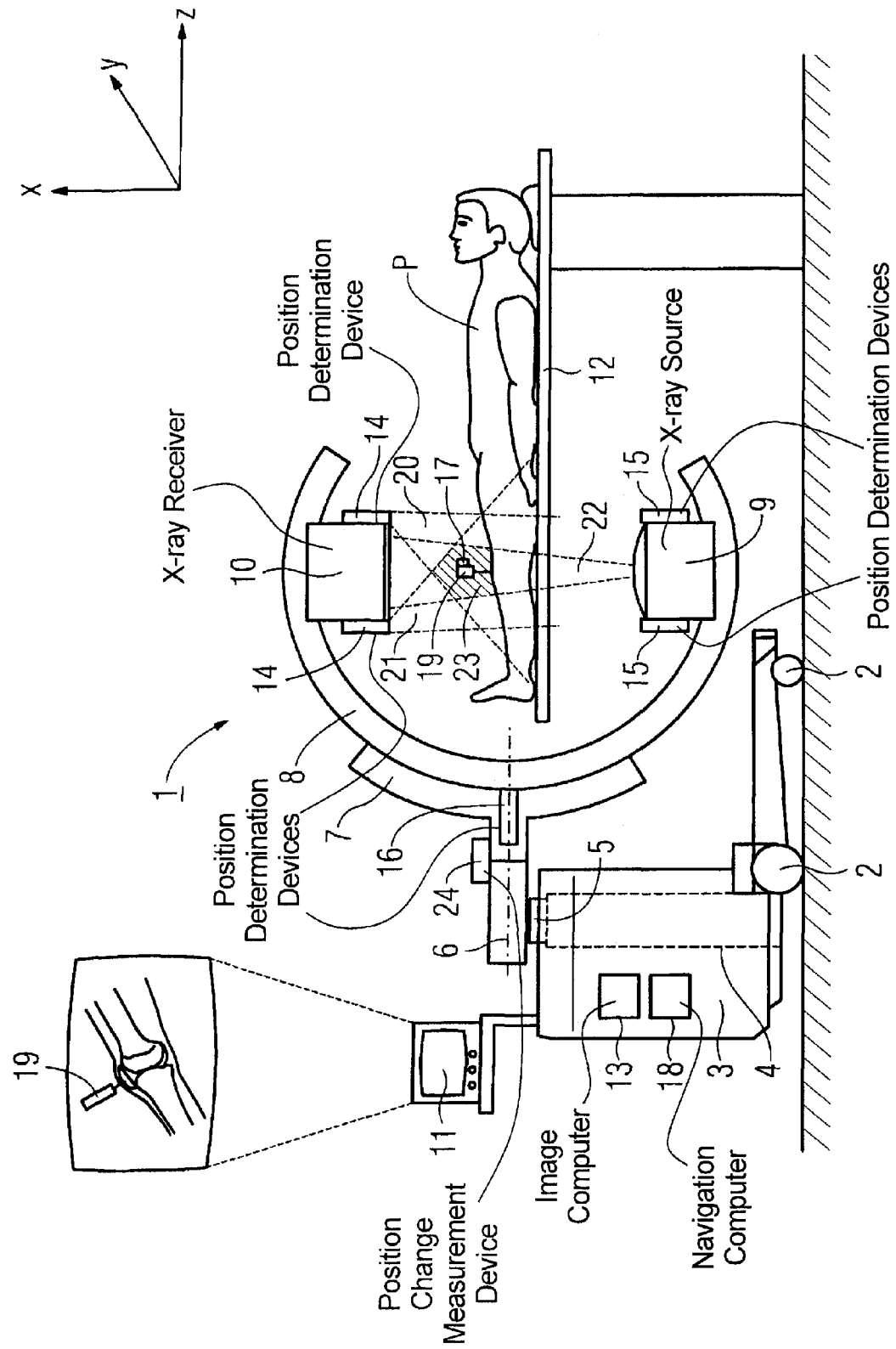

MEDICAL APPARATUS WITH IMAGE ACQUISITION DEVICE AND POSITION DETERMINATION DEVICE COMBINED IN THE MEDICAL APPARATUS

BACKGROUND OF THE INVENTION

1. Field of the Invention

The present invention concerns a medical apparatus for implementation of operative procedures on a patient with image acquisition device and position determination device combined in the medical apparatus.

2. Description of the Prior Art

During operative procedures on a patient, the control of surgical instruments (such as, for example, laparoscopes, endoscopes, needles, etc.) often ensues by means of various image-supported methods.

In the simplest case, purely image-supported positionings of medical instruments are implemented, meaning that the instrument position is directly visible and can be tracked in the image. Examples of this are the needle guidance (for example for biopsies or RF ablations) by means of ultrasound, CT fluoroscopy or x-ray fluoroscopy. These methods are characterized by real-time capability and are standards today in specific application fields.

Another widespread method is the use of surgical navigation based on preoperative images. In this case the positioning of the instruments is implemented with the assistance of navigation systems on the basis of image data that were acquired before the actual operation on the patient. The image data are normally based on CT or MR images; but, SPECT (Single Photon Emission Computed Tomography) or PET (Positron Emission Tomography) images are also increasingly used. An example of the implementation of methods based on preoperative images the use of is robotics in orthopedics or neurosurgery. Operations on the knee and on the hip are also examples of a robot-supported operative procedure. Conventionally, such procedures are implemented exclusively using CT x-ray images of the region to be operated upon that are acquired before the operative procedure.

Other procedures, however, which can lead to a position change or position changes, require continuous monitoring images during the procedure in order to ensure a reliable positioning of the medical instruments, and therewith a safe implementation of the operation. In this case navigation and imaging are combined during the procedure, with new (updated) images of the patient being acquired as needed during the operation (for example after bone reduction (realignment of a fractured bone), after tissue removal (extraction) and after physical changes in position) and are provided to the navigation so that this can always be based on current image data. The use of such a medical method to support operative procedures on a patient is also useful when the surgeon is blocked from the viewing of the working end of a medical instrument directed by him or her and penetrating into the body of the patient and/or when a correlation between a position and shape of a body part or an organ shown in an image acquired beforehand, and the actual position and shape of the body part or organ is not available during the operation. Such an absence of correlation can occur either because the position of the patient during the operation on a patient bed does not precisely correspond to the position of the patient in the preoperative image acquisition or because, for example, deformations of body parts, deformations of organs or variations of organ positions occur due to natural movements (for example heartbeat, respiration, peristalsis).

The navigation system thus serves for the precise determination of the spatial coordinates, i.e. the position and orientation of the instrument in space or at an operation site. The image of the instrument should be mixed as accurately as possible into an image acquired with the image acquisition system. Multiple camera systems (for example CCD (charge coupled device) cameras) are often used as detection sensors in the position determination device of the navigation system, but other sensors that operate on electromagnetic principles are also conceivable. Ultrasound methods, although generally conceivable, rarely play a role any more today due to their disadvantages with regard to reflections and temperature dependency. The navigation systems, in particular the position determination device with its detection sensors, normally can be freely positioned in the operating room. In any case, however, the position determination device is designed separate from the image acquisition device. This must in many cases be perceived as a disadvantage since there must be good compatibility between the image acquisition device and the position determination device. For example, in order to enable such a navigation-directed procedure it is necessary to produce a mathematical relation in the form of a coordinate transformation between the coordinate system of the image information of the patient, or the coordinate system of the reconstructed volume of the patient, and the coordinate system of the sensors of the position determination device acquiring the medical instruments.

A device for determination of a coordinate transformation for navigation-directed procedures is known for a C-arm x-ray apparatus from DE 199 17 867. The known device has an adapter with markers that can be detected by a navigation system as well as a reference structure with x-ray-positive markings. A coordinate transformation between a coordinate system associated with the navigation system and a coordinate system associated with the x-ray image can be produced using the reference structure and the adapter. Sometimes identifiers (artificial markers) that are artificially arranged on the patient, or anatomically-dependent markers (such as, for example, distinctive bone structures) are used as markers. The markers must therefore normally be approached individually and in the correct order with the instrument in order to be able to determine the coordinate transformation between the two coordinate systems.

DE 102 10 287 provides a method for marker-less registration for navigation-directed procedures. According to this method, coordinate systems are assigned to an x-ray calibration phantom and the mounting of the x-ray apparatus. Coordinate transformations between the two coordinate systems then can be produced with acquisitions and evaluations of 2-D projections of the x-ray calibration phantom.

In both aforementioned documents, the position determination device of the navigation system and the image acquisition device are separate from one another; the imaging x-ray apparatuses are mobile. Each relative movement between the navigation system and the x-ray apparatus either involves a new calibration or is taken into account by the use of reference markers that, for example, are mounted on the operating table.

Freely-positionable position determination devices (thus essentially the sensors for navigation systems) are mounted in the operating room, normally at some distance from the operation region. This has the disadvantage that the sensitive volume (thus the acquired region) is relatively large, which in turn entails disadvantages in the resolution of the sensors. Furthermore, other components (such as, for example, markers) to be acquired by the position determination device must be designed correspondingly large in order to be reliably detected. In some cases it can even lead to occlusion (blocking) of sensors, for example by the treating operation team, or at least to a certain limitation of their freedom of movement.

A medical system with an imaging system and a navigation system is described in DE 199 51 503, wherein navigation system is "informed" of the usage of a movable C-arm x-ray apparatus. This movable C-arm x-ray apparatus is to be brought to a patient simply and quickly as needed for the purpose of the necessary image acquisitions for a navigation-directed procedure and can be removed again in the event that it is no longer required. The navigation system itself is, as noted above, arranged separately in the operating room with its position determination devices. The aforementioned disadvantages with regard to calibration of imaging hardware and the navigation hardware that also exist.

SUMMARY OF THE INVENTION

An object of the present invention is to provide a medical apparatus having an image acquisition device and a position determination device, combined therein that links, in a simple manner, the imaging components and position determination components (the navigation hardware).

The above object is achieved in accordance with the invention by a medical apparatus for acquisition of images of at least one region of the body of a patient by means of an image acquisition device, with at least one position determination device that serves for determination of the position of at least one medical instrument within an operation region being arranged at the medical apparatus. By the arrangement of the position determination device at the medical apparatus and therewith the fixed connection of the position determination device with the medical apparatus, the need for additional configuration, reconfiguration or alignment of the position determination device is avoided. Due to the fixed connection, the position determination device of the navigation system and the image acquisition device are also no longer subjected to an uncontrolled relative movement relative to one another. The coordinate transformation that is implemented one time between the coordinate system of the position determination device and the coordinate system of the image acquisition system thus can be retained. A repeated calibration procedure after a spatial variation of the medical apparatus can be entirely omitted. The position determination device is mounted on the medical apparatus such that its sensors have an unobstructed detection area (field of view) at the operation region. This is normally already achieved by a free, non-limited view (thus a view that is not occluded or blocked by other objects that are not transparent for the sensor) being enabled at the site of the intervention.

The sensors of the position determination device can be based on optical, magnetic, ultrasound-based, radio-based or infrared-based sensing techniques Mixed forms of these techniques can also be advantageously used, such mixed forms in combination increasing the precision of the position determination of the medical instruments and improving the failure susceptibility due to possibly redundant systems. It is thus possible to use some optical sensors (which are normally CCD cameras) and to supplement these with sensors that, for example, are based on a magnetic position determination method. It would also be conceivable to supplement optical systems with systems that operate on the basis of measurements of the reflections produced by the medical instruments. With the integration of the position determination device into the medical apparatus, these will inevitably be positioned closer to the actual operation region than is the case given the conventional separate systems, and new possibilities for use of position-determining sensors therewith result. Other position determination methods (for example infrared) can also result from this arrangement that are not yet used today due to the greater separation (distance) between operation region and the position determination device. Due to the smaller separation from the operation field, the position determination device can naturally also be designed much smaller, lower-power and thus also normally more cost-effectively. Additional navigation hardware in the operating room can be foregone due to the integration of the position determination device into the medical apparatus, The position determination device is positioned closer to the operation field so the visibility of the medical instruments to the navigation hardware is distinctly improved. The operating team can move more freely without significantly limiting the visibility of the medical instruments with their bodies.

In a preferred embodiment the position determination device has at least two sensors that cover an overlapping detection region in the operation field. In this case a stereoscopic detection of the medical instrument can be ensured with the position determination device, so the position change of the medical instrument in space can be detected in order to mix this position change into image data sets of the patient from the operation region.

In a further embodiment, the position determination device overlays the detection region of the sensors with the acquisition region of the image acquisition device in the operation region. As already mentioned, navigation methods are often used for navigation of medical instruments in preoperatively-acquired image data sets of the patient. In this variant an adjustment with 2D or 3D image data sets is now enabled, which 2D or 3D image data sets have been acquired with the image acquisition device of the medical apparatus itself and/or during the intervention. Further exposures for quality control of the intervention can easily be acquired in this manner and possibly be compared with preoperative image data sets and the position of the medical apparatus.

In a preferred embodiment, the medical apparatus has at least one measurement device with which a sufficiently-precise position change of the image acquisition device or position determination device or of image acquisition device and position determination device can be detected in space. This is particularly advantageous where a movement of the coordinate systems relative to one another nevertheless arises due to the selected, fixed arrangement of the position determination device via the determined use of the image acquisition device of the medical apparatus (for example adjustment to the operation region, 3D acquisitions at various acquisition angles). In some cases medical devices for measurement of displacement or rotation are integrated anyway into conventional medical apparatuses for acquisition of images of a patient (for example rotation deflection of a C-arm x-ray apparatus). In these cases these values are used as needed under the circumstances.

In the aforementioned embodiment this relative movement (that has been made measurable by suitable and generally known sensors) can be provided by the measurement device as an output signal. This signal can then serve as an input signal to a computational correction device incorporated into the updating (tracking) of the coordinates as a parameter of a coordinate transformation. A correlation between the position change of the imaging apparatus position determination components thus can be established at any time without having to implement a recalibration of the overall system. It is generally known that geometric deformations dependent on the position of the acquisition device (for example C-arm) can occur due to rotation of the acquisition device (for example of a C-arm x-ray apparatus) given use of imaging medical apparatuses. Such deformations can cause deflections of up to a few cm and will lead to an error in the coordinate transformation in these circumstances. However, tests have also shown that these deformations are often reproducible. Further position-dependent parameters for the correction device (which parameters are taken into account in the aforementioned calculation model of the coordinate transformation) can be empirically found given knowledge of the position change of the image acquisition device and/or the position determination device. Intensive tests on the subject of deformations, in particular on C-arm apparatuses, have likewise shown that such deformations that are not reproducible do in fact occur, but their influence is normally so small that these incur tolerable (only because they occur within narrow limits) errors. Nevertheless, such non-reproducible deformations are also detectable, for example, by comparing deformation-free reference images, which were acquired with fixed optical markers, with the images in the conventional operation. Either correction variables for the coordinate transformation can then be determined, or only error messages can be derived from this desired/real comparison, in particular with regard to the position displacement of the optical markers.

In another preferred embodiment, at least one position determination device is permanently connected with the image acquisition device. The advantage of such an embodiment is that a relative movement between the image acquisition device and the position determination device no longer results upon a readjustment of the image acquisition device, for example to the operation region. This can avoid the necessity of measurement devices being provided at such systems, to measure displacement of the coordinate systems of the position determination device and the image acquisition device that inevitably occurs due to the arrangement of the position determination device and due to the conventional use of the medical apparatus.

In a further embodiment, the medical apparatus is an x-ray apparatus. This offers the advantage that it normally can be moved or arbitrarily positioned around a patient bed and thus can be used as needed for an operation. The placement relationships of the operation team are therefore only insignificantly limited. X-ray apparatuses therewith offer an ideal example of application for the invention since precisely this spatial variability can be used without a new calibration of the navigation system having to be implemented. X-ray apparatuses can provide both 2-D and 3-D images due to the downstream image construction and therewith can likewise offer ideal conditions for navigation-directed procedures. Position determination devices are advantageously mounted in pairs on the x-ray source and possibly additionally in pairs on the x-ray detector. When necessary, however, more than two sensors can be arranged at the x-ray source or at the x-ray detector. In each case a free, unoccluded acquisition region at the operation region should be possible. Furthermore, the display devices (respectively mounted in pairs) should also be arranged at a certain distance from one another at the x-ray detector in order to ensure a stereoscopic acquisition of the operation field, in particular of the medical instruments in the operation field. This condition is normally already fulfilled by the position determination devices being arranged on the opposite sides of the x-ray detector. From the localization of the position determination devices (for example, as proposed, on both sides of the x-ray detector and additionally, for example, on both sides of the x-ray source) a monitoring of the operation region and the medical instruments located therein is ensured at all times during rotation of the x-ray apparatus around its Z-axis.

In a further embodiment the medical apparatus is a C-arm apparatus and at least one position determination device is located offset relative to the x-ray source on a mounting device of the C-arm. One or more further position determination devices are therewith mounted on the mounting device of the C-arm apparatus in addition to the aforementioned position determination device, such that the further position determination devices have a spatially offset detection region at the operation region relative to the other position determination device. This arrangement is advantageous because the sensors of the position determination device are spatially very close to the operation region, but occlusions due to body parts of the operation team can be precluded to a large extent.

In a further embodiment of the invention, a position determination device is arranged essentially 90° offset relative to the x-ray source. This position determination device is therewith located in proximity to the rotation axis of the C-arm. A transverse displacement of the coordinate systems of position determination device and image acquisition device therewith does not occur; the pure rotation deflection of the C-arm thus can be measured relatively simply and be definition to the correction device for coordinate transformation. The sensors of this position determination device and the sensors of the position determination device of the image acquisition device exhibit a substantially rectangular offset. Due to this angle offset between the position determination devices, the precision in the detection of position changes of the medical instruments can be increased since a position change in the detection direction of the position determination components can be resolved only with a minimal path change; this can then be perceived as a maximum path change by the other position determination devices offset by 90°.

In a preferred embodiment a display unit for graphical representation and means for mixing an image of the medical instruments into the acquired images of the body of the patient are associated with the medical apparatus. One or more high-resolution monitors are normally used as a display unit. The components for mixing the image of the medical instrument into the acquired images basically include markers, image computers and navigation computers. In the ideal case the display elements and the mixing components are arranged in or at the medical apparatus itself, such that the medical apparatus likewise represents the medical image-supported operation system. In a different version the medical apparatus should have the necessary interfaces so that external display units and/or image or, respectively, navigation computers can be connected to the medical apparatus without further measures.

DESCRIPTION OF THE DRAWINGS

The single FIGURE schematically shows an example of a C-arm x-ray apparatus with integrated position determination device in accordance with the invention.

DESCRIPTION OF THE PREFERRED EMBODIMENTS

A C-arm x-ray apparatus 1 with an apparatus cart 3 that can be moved on wheels 2 is schematically shown in FIG. 1. A lifting device 4 (schematically indicated) with a column 5 that serves for displacement of the mounting part 6 along the rotation axis z runs within the apparatus cart 3. A mounting device 7 that accommodates the C-arm 8 is mounted on the mounting part 6. The connection of the mounting device 7 with the mounting part 6 allows a rotation of the C-arm 8 connected with the mounting device 7. An x-ray source 9 and an x-ray receiver 10 are mounted opposite one another on the C-arm 8. The x-rays emitted from the x-ray source and striking the x-ray receiver 10 form the acquisition region 22 of the x-ray radiation.

In the exemplary embodiment, the x-ray receiver 10 is a known solid-state detector. The x-ray images acquired with the x-ray detector can be shown in a known manner on a display device 11. The C-arm x-ray apparatus 1 shown in FIG. 1 allows the production of 3D x-ray images of the body or of body parts of a patient P supported on a vertically and horizontally adjustable patient bed 12 in the acquisition region 2.

An image computer 13 (arranged in the apparatus cart 3 of the C-arm x-ray apparatus 1 in the exemplary embodiment), connected (in a manner not shown) with the solid-state detector 10 and the display unit 11, is present for 3D imaging. The image computer 13 reconstructs the 3D images of the body part of the patient P to be represented, which reconstruction is made in a known manner from 2D projections that are acquired given a displacement of the C-arm around the Z-axis. With the aid of the navigation system of the medical apparatus (essentially comprising the position determination devices 14, 15, 16 and the navigation computer 18), during the operation on the patient P instruments 19 used by a surgeon (not shown in the FIGURE) can be mixed as an image into the 3D images of the body of the patient P that are produced during the operation and reconstructed by the image computer 13 and displayed on the display unit 11. In this manner the surgeon receives an effective and reliable support in the operative procedure. This is primarily advantageous when the view of the working end of the instrument 19 that has penetrated into the body tissue is not visible to the surgeon, for example upon penetration of the instrument 19 into the body tissue of the patient P, and no precise knowledge as to how far the instrument 19 has already penetrated into the body of the patient P, or what the position of the instrument 19 is relative to an organ of the patient P, exists. In such a case the surgeon can recognize the position and orientation of the instrument 19 using the mixings of the image of the instrument 19 into an acquired 3D image of the body or a body part of the patient P, and can correspondingly navigate the instrument 19. In the present exemplary embodiment the position determination devices 14 are mounted on both sides of the x-ray detector 10 and are permanently connected with this, such that a rotation of these position determination devices is not possible. Each of the position determination devices 14 has a free, unoccluded detection view 20, 21 of the operation field and the medical instruments 19. The detection regions of the position determination devices 20 and 21 overlap in a wide area, however at least in the direct operation field of the patient P. The sub-region of this overlap area composed of detection regions 20 and 21, which overlap area overlaps with the detection region of the x-ray radiation 22, forms the detection region 23 in which the aforementioned detection regions (20, 21, 22) overlap. The position determination device 15 is mounted at the x-ray source 9 in the same manner as mentioned previously. The detection regions of this position determination device can form the overlapped detection region 23 either instead of the detection regions (20, 21) or in addition to these.

In the exemplary embodiment, at least one first position determination device 16 is permanently connected with the mounting device 7. In the exemplary embodiment the position determination device 17 is mounted in proximity to the rotation axis of the C-arm. Other positions on the mounting device 7 are also possible. With regard to its detection region, the preceding statements regarding the detection regions of the position determination devices 14, 15 are equivalent.

Optical sensors are normally used in the position determination devices 14, 15 and 16, however other sensors based on other physical principles are also conceivable. In addition to the position determination devices, the navigation system furthermore comprises reference elements or markers which are arranged at instruments or objects that should be detected in terms of position and are detected by the position determination devices 14, 15 and 16. Reference element 17 is shown as an example. At least three of these reference elements are required for the coverage of the function and all six degrees of freedom (triangulation). Today passive optical markers with infrared-reflecting surfaces are advantageously used since with these additional (normally interfering) cabling can be omitted. A navigation computer 18 (likewise belonging to the navigation system) evaluates the images acquired with the position determination devices 14, 15 and 16 and can determine the positions (i.e. the bearings and orientations) of the reference elements 17 (and thus of the medical instruments 19) in space using the detected reference elements 17. The navigation computer 18 is connected with the image computer 13 in a manner not shown. The navigation computer 18 respectively provides the data about the current positions of the medical instruments 19 to the image computer 13, such that the image computer 13 can determine the exact position and orientation of the medical instrument 19 relative to the operation site, and can mix the image of the medical instrument 19 into an image acquired with the C-arm x-ray apparatus 1 during the operation. This image is then made visible on the display unit 11. In the case where a position variation of the image acquisition device relative to the position determination devices results due to a position change of the image acquisition device by adjustment to the body part to be examined or during 3D acquisitions, measurement devices are also provided that measure the position variations of the imaging components. In the exemplary embodiment described here, the rotation of the C-arm is measured by the measurement device 24. These position changes are provided to the components implementing the coordinate transformation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical apparatus comprising:
   a C-arm x-ray apparatus comprising a plurality of components configured to operate to acquire an image of a region of a body of a patient located in an acquisition region of the C-arm x-ray apparatus, said plurality of components including a C-arm that is movable through a plurality of different positions and that exhibits a predictable mechanical deformation in at least one of said positions;
   at least one position determination device configured to determine a position of a medical instrument adapted to interact with the body of the patient in an interaction region located within said acquisition region, said at least one position determination device being fixedly attached to a component among said plurality of components of said C-arm x-ray apparatus, the fixed attachment of said at least one position determination device to said component producing a known relationship between position coordinates of said C-arm x-ray apparatus in a defined coordinate system and position coordinates of said at least one position determination device in said defined coordinate system;

a measurement device that identifies when said C-arm is in said at least one of said positions by emitting a measurement device signal; and a computer supplied with said measurement device signal and with an image of said region of the body of the subject acquired by said C-arm x-ray apparatus, said computer comprising a display screen and being configured to mix an image of said instrument into said image of said region of the body of said patient in a positionally accurate mixing at said display screen, using said position of said instrument obtained by said at least one position determination device, and said computer being configured to update said known relationship between the position coordinates of said C-arm x-ray apparatus and the position coordinates of said at least one position determination device, dependent on said measurement device signal, to update said known relationship, when said C-arm is in said at least one of said positions, dependent on said predicted mechanical deformation, to obtain an updated relationship, and to use said updated relationship to maintain said positionally accurate mixing despite said C-arm exhibiting said predictable deformation in said at least one of said positions.

2. A medical apparatus as claimed in claim 1 wherein said at least one position determination device comprises at least two sensors each having a detection region, said at least two sensors being mounted to said component of said C-arm x-ray apparatus with the respective detection regions thereof overlapping in said interaction region.

3. A medical apparatus as claimed in claim 2 wherein said overlapping detection regions of said at least two sensors also overlap said acquisition region of said C-arm x-ray apparatus.

4. A medical apparatus as claimed in claim 1 wherein said at least one position determination device is permanently attached to said component of said C-arm x-ray apparatus.

5. A medical apparatus as claimed in claim 1 wherein said plurality of components of said C-arm x-ray apparatus further include an x-ray detector and an x-ray source, and wherein said at least one position determination device comprises sensors mounted on at least one of said x-ray source and said x-ray detector.

6. A medical apparatus as claimed in claim 1 wherein said plurality of components of said C-arm x-ray apparatus further include a mounting device for said C-arm and an x-ray source on said C-arm, and wherein said at least one position determination device is mounted offset from said x-ray source on said mounting device.

7. A medical apparatus as claimed in claim 6 wherein said at least one position determination device is offset by 90° relative to said x-ray source.

* * * * *